US00PP31538P2

(12) United States Plant Patent
Daido et al.

(10) Patent No.: US PP31,538 P2
(45) Date of Patent: Mar. 10, 2020

(54) ***PETUNIA* PLANT NAMED 'MIPEHR436'**

(50) Latin Name: ***Petunia* X *hybrida***
Varietal Denomination: MIPEHR436

(71) Applicants: Genya Daido, Shizuoka (JP); Hirotaka Oya, Sunto-Gun (JP)

(72) Inventors: Genya Daido, Shizuoka (JP); Hirotaka Oya, Sunto-Gun (JP)

(73) Assignee: Miyoshi + Co., Ltd., Tokyo (JP)

( * ) Notice: Subject to any disclaimer, the term of this patent is extended or adjusted under 35 U.S.C. 154(b) by 0 days.

(21) Appl. No.: 16/350,880

(22) Filed: Jan. 28, 2019

(51) Int. Cl.
*A01H 5/02* (2018.01)
*A01H 6/82* (2018.01)

(52) U.S. Cl.
USPC ..... Plt./356.12
CPC ..... *A01H 6/824* (2018.05)

(58) Field of Classification Search
USPC ..... Plt./356.12
CPC ..... A01H 6/824; A01H 5/02
See application file for complete search history.

*Primary Examiner* — Keith O. Robinson
(74) *Attorney, Agent, or Firm* — C. A. Whealy

(57) ABSTRACT

A new and distinct *Petunia* plant named 'MIPEHR436', characterized by its upright to outwardly spreading and mounding plant habit; moderately vigorous to vigorous growth habit; freely branching habit; freely flowering habit; double type flowers that are red purple in color with white-colored margins; and good garden performance.

2 Drawing Sheets

Botanical designation: *Petunia* X *hybrida.*
Cultivar denomination: 'MIPEHR436'.

BACKGROUND OF THE INVENTION

The present invention relates to a new and distinct cultivar of *Petunia* plant, botanically known as *Petunia* X *hybrida* and hereinafter referred to by the name 'MIPEHR436'.

The new *Petunia* plant is a product of a planned breeding program conducted by the Inventors in Nagaizumicho, Shizuoka, Japan. The objective of the breeding program is to create new freely-flowering *Petunia* plants with double bi-colored flowers and good garden performance.

The new *Petunia* plant originated from a cross-pollination made by the Inventors in August, 2015 in Nagaizumicho, Shizuoka, Japan of a proprietary selection of *Petunia* X *hybrida* identified as code number P27-271-1, not patented, as the female, or seed, parent with a proprietary selection of *Petunia*X *hybrida* identified as code number P27-655-1, not patented, as the male, or pollen, parent. The new *Petunia* plant was discovered and selected by the Inventors as a single flowering plant within the progeny of the stated cross-pollination in a controlled greenhouse environment in Nagaizumicho, Shizuoka, Japan in August, 2016.

Asexual reproduction of the new *Petunia* plant by in vitro meristem culture in a controlled greenhouse environment in Nagaizumicho, Shizuoka, Japan since April, 2017 has shown that the unique features of this new *Petunia* plant are stable and reproduced true to type in successive generations.

SUMMARY OF THE INVENTION

Plants of the new *Petunia* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'MIPEHR436'. These characteristics in combination distinguish 'MIPEHR436' as a new and distinct *Petunia* plant:

1. Upright to outwardly spreading and mounding plant habit.
2. Moderately vigorous to vigorous growth habit.
3. Freely branching habit.
4. Freely flowering habit.
5. Double type flowers that are red purple in color with white-colored margins.
6. Good garden performance.

Plants of the new *Petunia* can be compared to plants of the female parent selection. In side-by-side comparisons, plants of the new *Petunia* differ primarily from plants of the female parent selection in the following characteristics:

1. Plants of the new *Petunia* have larger flowers than plants of the female parent selection.
2. Plants of the new *Petunia* have double type flowers whereas plants of the female parent selection have single type flowers.

Plants of the new *Petunia* can be compared to plants of the male parent selection. In side-by-side comparisons, plants of the new *Petunia* differ primarily from plants of the male parent selection in flower color as plants of the new *Petunia* have red purple-colored flowers with white-colored margins whereas plants of the male parent selection have blue-colored flowers with white-colored margins.

Plants of the new *Petunia* can be compared to plants of *Petunia* X *hybrida* 'Kuroshinju', not patented. In side-by-side comparisons, plants of the new *Petunia* differ primarily from plants of 'Kuroshinju' in the following characteristics:

1. Plants of the new *Petunia* are slightly taller than plants of 'Kuroshinju'.

2. Leaves of plants of the new *Petunia* are broader than leaves of plants of 'Kuroshinju'.
3. Flowers of plants of the new *Petunia* are red purple in color with white-colored margins whereas flowers of plants of 'Kuroshinju' are dark purple in color with pale yellow-colored margins.

BRIEF DESCRIPTION OF THE PHOTOGRAPHS

The accompanying colored photographs illustrate the overall appearance of the new *Petunia* plant showing the colors as true as it is reasonably possible to obtain in colored reproductions of this type. Colors in the photographs may differ slightly from the color values cited in the detailed botanical description which accurately describe the colors of the new *Petunia* plant.

The photograph on the first sheet is a side perspective view of a typical flowering plant of 'MIPEHR436' grown in a container.

The photograph on the second sheet is a close-up view of a typical flowering plant of 'MIPEHR436'.

DETAILED BOTANICAL DESCRIPTION

The aforementioned photographs and following observations and measurements describe plants grown during the summer in 12-cm containers in a polyethylene-covered greenhouse in Fukuroishi, Shizuoka, Japan and under cultural practices typical of commercial *Petunia* production. During the production of the plants, day temperatures averaged 30° C., night temperatures averaged 20° C. and light levels averaged 80,000 lux. Plants were seven weeks from planting rooted cuttings when the photographs and description were taken. In the following description, color references are made to The Royal Horticultural Society Colour Chart, 2015 Edition, except where general terms of ordinary dictionary significance are used.

Botanical classification: *Petunia* X *hybrida* 'MIPEHR436'.

Parentage:

*Female, or seed, parent.*—Proprietary selection of *Petunia* X *hybrida* identified as code number P27-271-1, not patented.

*Male, or pollen, parent.*—Proprietary selection of *Petunia* X *hybrida* identified as code number P27-655-1, not patented.

Propagation:

*Type.*—By in vitro meristem culture.

*Time to initiate roots, summer.*—About one week at soil temperatures about 20° C. and ambient temperatures ranging from 20° C. to 30° C.

*Time to initiate roots, winter.*—About one week at soil temperatures about 20° C. and ambient temperatures ranging from 10° C. to 20° C.

*Time to produce a rooted young plant, summer.*—About four weeks at soil temperatures about 20° C. and ambient temperatures ranging from 20° C. to 30° C.

*Time to produce a rooted young plant, winter.*—About five weeks at soil temperatures about 20° C. and ambient temperatures ranging from 10° C. to 20° C.

*Root description.*—Fine, fibrous; typically white in color, actual color of the roots is dependent on substrate composition, water quality, fertilizer type and formulation, substrate temperature and physiological age of roots.

*Rooting habit.*—Freely branching; medium density.

Plant description:

*Plant and growth habit.*—Upright to outwardly spreading and mounding plant habit; freely branching habit with about six primary lateral branches each with secondary lateral branches potentially developing at every node; dense and bushy appearance; pinching enhances development of lateral branches; moderately vigorous to vigorous growth habit; moderate growth rate.

*Plant height, soil level to top of foliar plane.*—About 8 cm.

*Plant height, soil level to top of floral plane.*—About 10 cm.

*Plant diameter* (*area of spread*).—About 20 cm.

*Lateral branches.*—Length: About 15 cm. Diameter: About 2 mm. Internode length: About 2 cm. Strength: Moderately strong. Aspect: Initially upright then outwardly spreading. Texture and luster: Densely pubescent; viscid; matte. Color, developing and developed: Close to 144B.

Leaf description:

*Arrangement.*—Alternate before flowering and after flowers develop; leaves simple.

*Length.*—About 4 cm.

*Width.*—About 3 cm.

*Shape.*—Ovate.

*Apex.*—Obtuse to rounded acute.

*Base.*—Attenuate.

*Margin.*—Entire.

*Texture and luster, upper and lower surfaces.*—Moderately pubescence; viscid; matte.

*Venation pattern.*—Pinnate, arcuate.

*Color.*—Developing leaves, upper surface: Close to 137C. Developing leaves, lower surface: Close to 143A. Fully expanded leaves, upper surface: Close to 137C; venation, close to 143A. Fully expanded leaves, lower surface: Close to 144A; venation, close to 137B.

*Petioles.*—Length: About 5 mm. Diameter: About 2 mm. Strength: Moderately strong. Texture and luster, upper and lower surfaces: Densely pubescence; viscid; matte. Color, upper and lower surfaces: Close to 144A.

Flower description:

*Flower type and flowering habit.*—Single axillary salverform flowers; flowers face upright to mostly outwardly; freely flowering habit with numerous flowers developing per plant during the flowering season.

*Natural flowering season.*—Long day responsive; long flowering period, plants flower from spring until the autumn, flowering continuous during this period; early flowering habit, plants begin flowering about six weeks after planting.

*Flower longevity on the plant.*—About ten days; flowers persistent.

*Fragrance.*—None detected.

*Flower buds.*—Length: About 3 cm. Diameter: Distally, about 1.8 mm; proximally, about 5 mm. Shape: Oblong, elongate. Texture and luster: Densely pubescent; viscid; matte. Color: Close to 1C.

*Flower diameter.*—About 5 cm.

*Flower depth* (*height*).—About 3.5 cm.

*Throat diameter, distal.*—About 1 cm.

*Tube length.*—About 5 mm.

*Tube diameter, proximally.*—About 5 mm.

*Petals.*—Quantity and arrangement: About 20 petals fused in several whorls; fused at the base. Petal lobe length (from throat): About 3.5 cm. Petal lobe width: About 2.5 cm. Petal lobe shape: Roughly spatulate. Petal lobe apex: Rounded acute; slightly undulate. Petal lobe margin: Entire; slightly undulate. Petal lobe texture and luster, upper surface: Smooth, glabrous; matte. Petal lobe texture and luster, lower surface: Sparsely pubescent; viscid; matte.

*Throat and tube texture and luster.*—Densely pubescent; viscid; matte.

*Color.*—When opening, upper surface: Close to 70A; towards the margins, close to NN155D. When opening, lower surface: Close to 63D; towards the margins, close to NN155D. Fully opened, upper surface: Close to N66B; towards the margins, close to NN155D; venation, close to N66D and NN155D; color becoming closer to NN74B and NN155D with development. Fully opened, lower surface: Close to 63D; towards the margins, close to NN155D; venation, close to N66D and NN155D; color becoming closer to 76C and NN155D with development. Flower throat (inside): Close to 62D; venation, close to 62D. Flower tube (outside): Close to 158C; venation, close to 157B.

*Sepals.*—Quantity and arrangement: Five sepals fused in a single star-shaped whorl. Calyx length: About 1.5 cm. Calyx diameter: About 1 cm. Length: About 1.5 cm. Width: About 3 mm. Shape: Ligulate. Apex: Rounded, blunt. Margin: Entire. Texture and luster, upper and lower surfaces: Densely pubescent; viscid; matte. Color: When opening and fully opened, upper surface: Close to 137B. When opening and fully developed, lower surface: Close to 138A.

*Peduncles.*—Length: About 3 cm. Width: About 1.5 mm. Strength: Moderately strong. Angle: About 20° from the stem axis. Texture and luster: Densely pubescent; viscid; matte. Color: Close to 144A.

*Reproductive organs.*—Stamens: Quantity per flower: Five. Filament length: About 2 cm. Filament color: Close to 157D. Anther size: About 1.5 mm by 2 mm. Anther shape: Bi-lobed. Anther color: Close to 154D. Pollen amount: None observed. Pistils: Quantity per flower: One; typically malformed. Pistil length: About 5 mm. Style length: About 1.8 mm. Style color: Close to 145B. Stigma diameter: About 1.5 mm. Stigma shape: Capitate. Stigma color: Close to 143C. Ovary color: Close to 143C.

*Seeds and fruits.*—To date, seed and fruit development has not been observed on plants of the new *Petunia*.

Pathogen & pest resistance: To date, plants of the new *Petunia* have not been noted to be resistant to pathogens or pests common to *Petunia* plants.

Garden performance: Plants of the new *Petunia* have been observed to have good garden performance and have been observed to tolerate rain, wind and temperatures ranging from about 5° C. to about 35° C.

It is claimed:

1. A new and distinct *Petunia* plant named 'MIPEHR436' as illustrated and described.

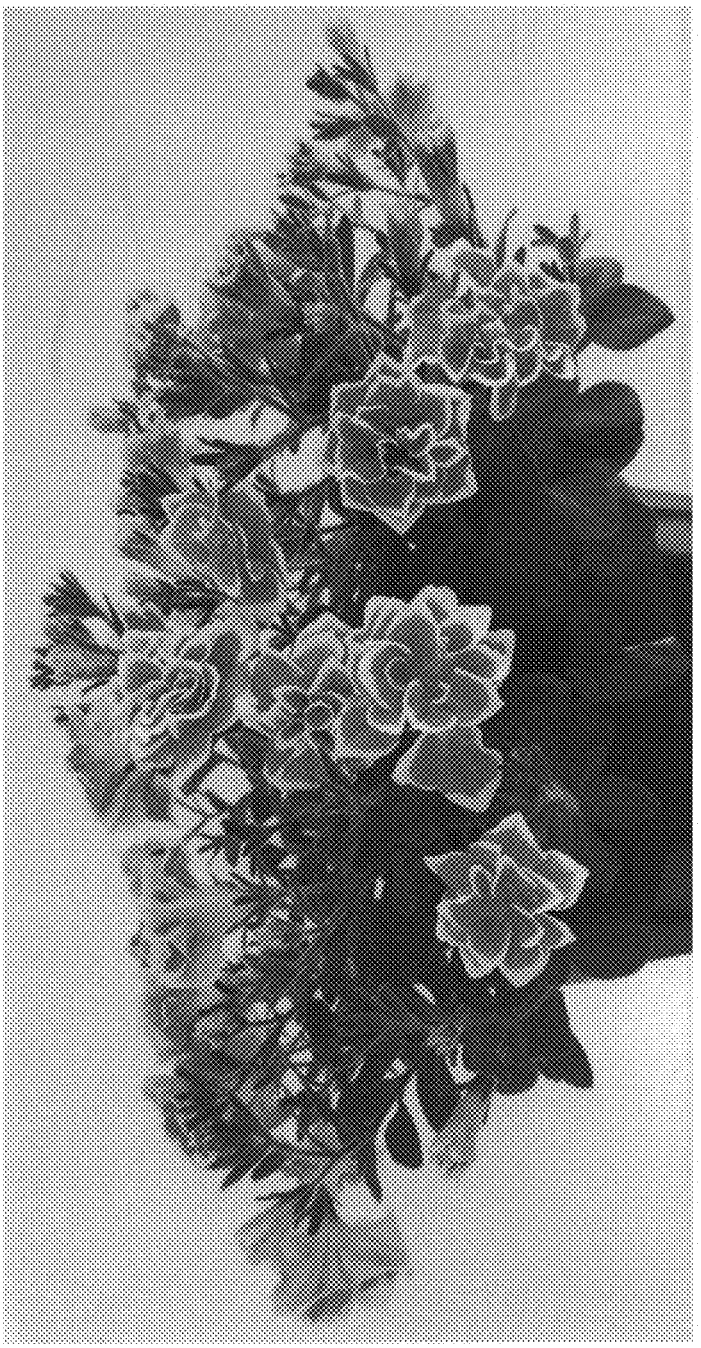

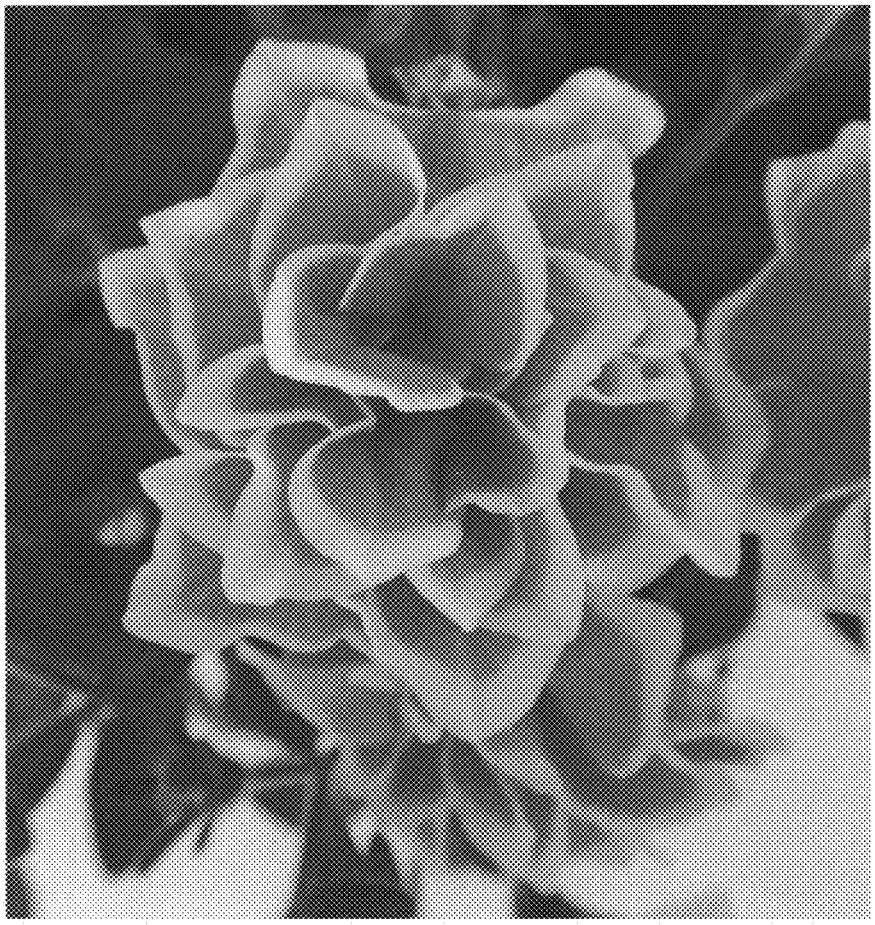

* * * * *